United States Patent [19]

Avejic

[11] Patent Number: 4,678,465
[45] Date of Patent: Jul. 7, 1987

[54] SANITARY PAD

[75] Inventor: Katarina Avejic, Chicago, Ill.

[73] Assignee: Dunromin Enterprises Unlimited, Inc., Chicago, Ill.

[21] Appl. No.: 817,538

[22] Filed: Jan. 10, 1986

[51] Int. Cl.⁴ .............................................. A61F 13/18
[52] U.S. Cl. .................................. 604/397; 604/393; 604/398
[58] Field of Search ............... 604/358, 385.1, 385.2, 604/386, 387, 388, 392, 393, 397, 398

[56] References Cited

U.S. PATENT DOCUMENTS

| | | | |
|---|---|---|---|
| 830,757 | 9/1906 | Williams | 604/397 |
| 1,041,420 | 10/1912 | Bornstein | 604/398 |
| 1,110,674 | 9/1914 | Rosiers | 604/398 |
| 1,447,367 | 3/1923 | Williams et al. | 604/398 |
| 1,508,740 | 9/1924 | Brand | 604/397 |
| 1,653,857 | 12/1927 | Kelley | 604/398 |
| 1,975,457 | 10/1934 | Heyman | 604/397 |
| 1,989,686 | 2/1935 | Deutsch | 604/398 |
| 3,654,927 | 4/1972 | Surpless | 604/397 |
| 3,970,087 | 7/1976 | Castaneda | 604/387 |

FOREIGN PATENT DOCUMENTS

| | | | |
|---|---|---|---|
| 845148 | 10/1938 | France | 604/393 |
| 395612 | 7/1933 | United Kingdom | 604/397 |

Primary Examiner—C. Fred Rosenbaum
Assistant Examiner—Denise Whelton
Attorney, Agent, or Firm—Hill, Van Santen, Steadman & Simpson

[57] ABSTRACT

An inexpensive washable reusable catamenial pouch or sanitary napkin pad is formed from a single sheet of absorbent fabric, such as flannel, into a generally rectangular strip with a bottom and folded over sides forming top flaps overlying the bottom. These flaps overlap each other along the length of the pouch at the longitudinal central portion of the bottom in a closed position of the pouch. Stitching secures together the flaps and bottom at each end of the pouch. The pouch is openable to receive liners such as impervious plastic and absorbent strips on the bottom thereof by lifting and spreading the flaps apart. Tapes extend from the ends of the pouch to be attached to a support belt or the like and when pulled away from the ends, the tapes are effective to close the pouch by pulling the top flaps into their overlapped position. The inserted absorbent liners may take the form of overlapped strips of the same material as the pouch and these strips may be pinned or otherwise secured to the bottom of the pouch.

13 Claims, 6 Drawing Figures

U.S. Patent  Jul. 7, 1987  4,678,465
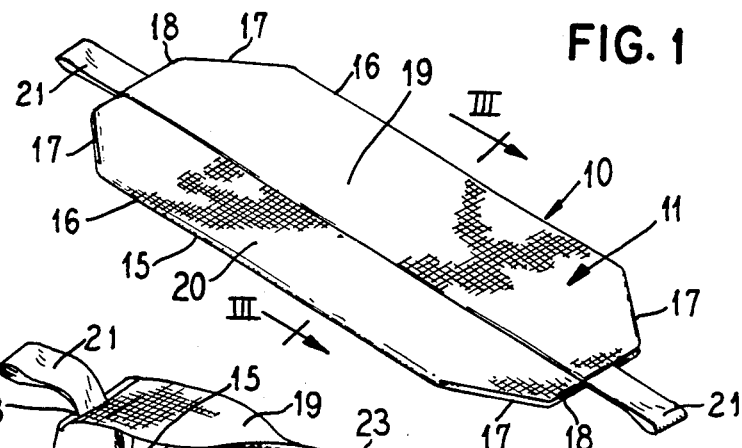
FIG. 1
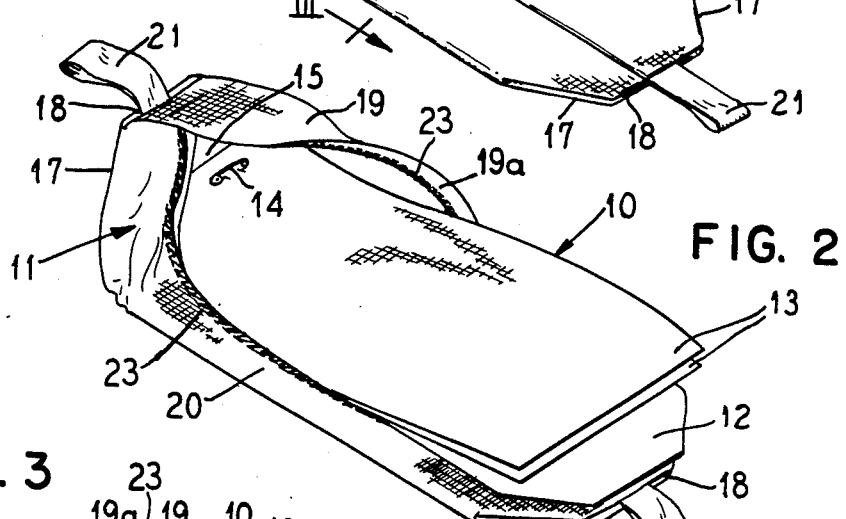
FIG. 2
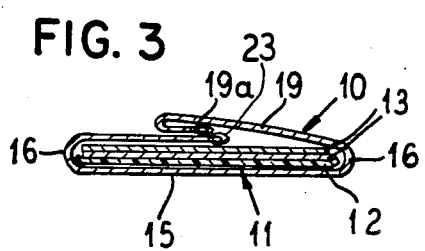
FIG. 3
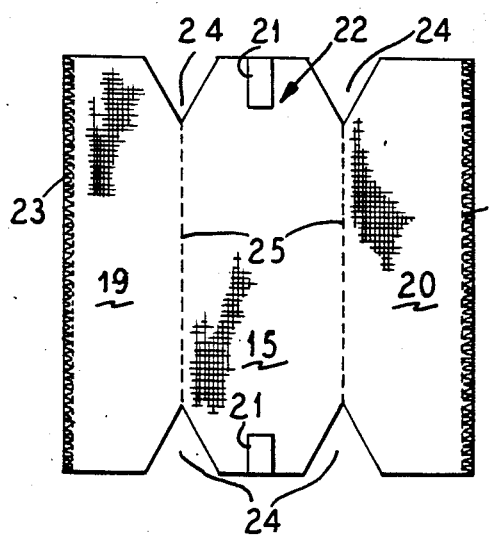
FIG. 4
FIG. 5
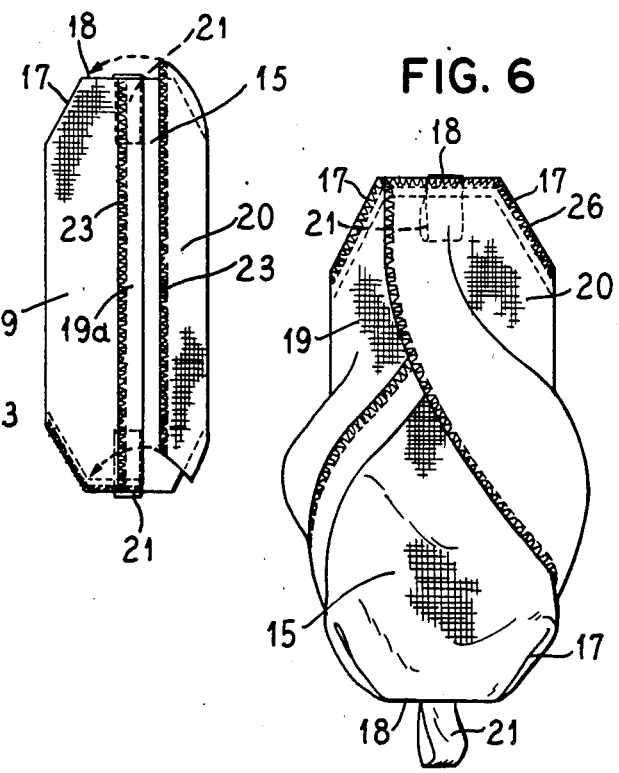
FIG. 6

4,678,465

SANITARY PAD

BACKGROUND OF THE INVENTION

1. FIELD OF THE INVENTION

This invention relates to sanitary napkins or catamenial pads which are washable and reusable and specifically relates to a reusable catamenial pouch of washable, absorbent material with an impervious liner strip overlying the bottom thereof and covered with additional absorbent material and having top flaps along its length which are spread apart to provide an open top bag and which overlap each other to close the pouch when its ends are pulled in opposite directions.

2. PRIOR ART

Conventional sanitary napkins or pads are disposable after single usage. In poor societies, such as in third world developing countries, the cost of such disposable napkins is prohibitive.

It would therefore be an improvement in this art to provide a fully sanitary washable reusable catamenial pad in the form of a pouch of washable absorbent fabric adapted to receive a sealing liner and additional absorbent material as needed and automatically closing when tensioned.

SUMMARY OF THE INVENTION

According to this invention, there is provided an inexpensive completely washable reusable sanitary napkin or catamenial pad in the form of a rectangular pouch with a bottom and folded over side flaps along the length of the bottom which, when spread apart, provide a bag-like recepticle to receive impervious liners and absorbent pad inserts and which, when tensioned, will overlap each other to close the pouch.

The pouch is formed from a single sheet of soft absorbent fabric, such as cotton flannel. This sheet is preferably about 10 inches long and about 7 inches wide. Its end edges are overlock stitched with the loops of the stitching overlapping the edges to prevent unravelling. Each side has a pair of V-shaped notches cut therein to a depth of about 1½ inches. Each notch has an included angle of about 60° so that the spaces between the notches and the spaces between the notches and ends of the sheet are each about 2 inches.

The ends of the sheet are folded over at the apexes of the opposed aligned adjacent notches thus providing flaps overlying a central rectangular base with tapered ends and with the stitched ends of the flaps being overlapped. The stitched edge of the underlying flap is folded back providing a margin about ½ inch wide. The folded over sheet then has a generally rectangular shape with tapered ends provided by the side edges of the overlapped notch portions. These overlapped tapered end portions are then overlock stitched together. Looped ribbon tapes about 1½ inches long are inserted to overlap the longitudinal central portion of the bottom of the pad and are also stitched to the ends.

The folded and stitched assembly is then turned inside out providing a generally rectangular bottom with parallel longitudinal side edges about 5¾ inches long having tapered end portions about 2 inches long and transverse end edges about 1¾ inches wide.

When the overlapped side flaps are spread apart an open top bag receptacle is provided having a bottom and upstanding sides and end walls provided by the flaps. The open pouch easily receives a liner and absorbent material on the bottom thereof. The liner is preferably a strip of moisture resistant impervious plastic material covering the bottom of the pouch. The absorbent material covers the liner and preferably takes the form of overlapped strips of washable absorbent material such as the same flannel-type fabric forming the pouch. The strips can be secured to the bottom with a safety pin, if desired, to prevent shifting during use. The pouch is automatically closed when the end tapes are pulled thereby bringing the side flaps into their overlapped position. These tapes are easily attached to a conventional support belt.

It will, of course, be understood that the above indicated dimensions are given only as an example for a preferred size pouch. These dimensions can vary substantially to provide small, medium or large sizes, as may be needed.

Both the pouch itself and the inserted strips are easily separately washed for subsequent sanitary reuse.

It is then an object of this invention to provide an inexpensive completely washable reusable catamenial pouch.

Another object of this invention is to provide a sanitary napkin pouch of absorbent material which is easily opened to receive additional absorbent material and is automatically closed when tensioned longitudinally.

A further object of the invention is to provide a catamenial pad formed from a single sheet of absorbent fabric material folded and stitched to provide a pouch with a generally rectangular bottom, folded over side flaps opening to provide a bag when spread apart and automatically closing in overlapped condition when tensioned.

A still further object of this invention is to provide a washable reusable catamenial pouch of soft absorbent fabric having overlapped side flaps adapted to be easily spread apart for forming an open top bag to receive a liner and additional absorbent material and having looped tapes projecting from the ends of the pouch for attachment to a support belt or the like and which, when tensioned, will automatically hold the pouch in closed position.

Other and further objects of this invention will be apparent to those skilled in this art from the following detailed description of the annexed sheet of drawings, which show a best mode embodiment of the invention.

ON THE DRAWINGS

FIG. 1 is a perspective top, side and end view of the pouch of this invention in closed position.

FIG. 2 is a perspective view similar to FIG. 1, but showing the pouch in opened position with liner strips being inserted in the opened pouch.

FIG. 3 is a transverse cross section of the pouch and liners along the line III—III of FIG. 1.

FIG. 4 is a plan view of the pattern for forming the pouch.

FIG. 5 is a preassembled folded top view of the pouch pattern with ribbon tabs inserted.

FIG. 6 is a view similar to FIG. 5, showing the end stitching and with one end of the pouch being turned inside out to form the finished pouch.

AS SHOWN ON THE DRAWINGS

The sanitary napkins or catamenial pads 10 of this invention shown in FIGS. 1–3 include a generally rectangular pouch 11 of soft washable absorbent material such as cotton flannel, an inserted impervious liner strip 12 preferably composed of plastics material, and one or more absorbent material strips 13 overlying the liner. The strips 12 and 13 are conveniently pinned in position on the bottom of the pouch 11 by a safety pin 14.

The pouch 11 has a flat rectangular bottom 15 with parallel side edges 16 having tapered ends 17 converging to transverse reduced width end edges 18.

The pouch 11 in its closed position of FIG. 1 has a flat top overlying the bottom and formed from folded over flaps 19 and 20 which overlap at the longitudinal central portion of the pouch. These flaps 19 and 20, when spread apart as shown in FIG. 2, open the pouch to provide an open top bag with the bottom 15 surrounded by an upstanding peripheral wall.

As shown in FIG. 3, the top flap 19 has a turned in marginal portion 19a along the free edge thereof to facilitate opening of the pouch to the FIG. 2 position.

Looped fabric tapes 21 extend from the transverse ends 18 of the pouch. When the strips 12 and 13 are tucked into the pouch on the bottom 15, the open pouch of FIG. 2 is automatically closed to the position of FIG. 1 by pulling the tapes 21. These tapes 21 are adapted to receive fastener hooks of a support belt or the like to support the pouch in its use position.

As shown in FIGS. 4–6, the pouch is formed from a single sheet 22 of absorbent fabric. This sheet is overlocked stitched at 23 along its end edges. Each side of the sheet 22 has a pair of V notches 24 cut therein. These notches are about equally spaced from each other and from the stitched edges 23 and provide fold lines 25 across the sheet terminating in the apexes of the notches. The sheet thus provides the central bottom 15 and the top flaps 19 and 20 of the pouch. The looped tapes 21 overlie the bottom portion 15 of the pad and top and bottom edges of the sheet.

As shown in FIG. 5, the flap 19 has its stitched end 23 folded back on top thereof to provide the folded over edge 19a. This flap 19 with its folded edge 19a is first folded along the line 25 over the bottom 15 and then the flap 20 is folded along its line 25 over the folded margin 19a of the flap 19.

As shown in FIG. 6, overlock stitching 26 secures together the tapered portions 17, the end edge portions 18 and the outer ends of the looped tapes 21. Then, as illustrated in FIG. 6, the sewed together assembly is turned inside out placing the stitching on the inside of the finished pouch and with the flap 19 becoming the outer flap overlying the flap 20. The outturned margin 19a of the flap 19 becomes the inturned margin illustrated in FIG. 3.

From the above descriptions is will therefore be understood that this invention now provides a completely sanitary reusable sanitary napkin or catamenial pouch which opens to form a bag recepticle for liner and absorbent material, which automatically closes when tensioned, and which of itself is absorbent and useful without liners. The number of liners can be selected as needed.

I claim as my invention:

1. A washable reusable catamenial pad which comprises a pouch folded and stitched from a single strip of absorbent fabric having a rectangular bottom with folded over sides forming two top flaps overlying the bottom and freely overlapping each other along the longitudinal central length of the top of the pouch in the close position of the pouch, stitching securing together the flaps and bottom only at each end of the pouch, said flaps between said stitched ends being separable to open into an open mouth closed bottom bag by lifting and spreading the flaps apart, an impervious removable liner strip in the pouch overlying the bottom of the pouch, a soft absorbent strip covering the liner strip in the pouch, tapes secured to and extending from the stitched ends of the pouch at the longitudinal central portion thereof effective to close the pouch when tensioned, and said tapes being looped to receive fasteners of a support belt.

2. A washable reusable catamenial pad which comrises a generally rectangular pouch of soft washable absorbent fabric having longitudinal folded over side providing two top flaps which overlap along the longitudinal central length of the top of the pouch in the closes position and which are easily spread apart to provide an open top bag adapted to receive liners on the bottom of the bag, said pouch having tapered ends converging to transverse end edges which when tensioned will pull the flaps into overlapped closed position.

3. The pad of claim 1 wherein the absorbent fabric is soft flannel.

4. The pad of claim 1 having tapered ends converging to the tapes.

5. The pad of claim 1 wherein the insert strips are pinned to the bottom.

6. The pad of claim 1 wherein the stitching is an overlocked stitch with loops lapping the edges of the fabric.

7. The pad of claim 2 wherein the overlapping top flap has an inturned marginal portion facilitating the spreading apart of the flap.

8. The pad of claim 2 having tapes extending from the transverse end edges of the pouch.

9. The method of making reusable catamenial pads which comprises cutting a pair of notches in each side of a rectangular sheet of washable soft absorbent fabric, aligning the apexes of each notch on opposite sides of the sheet, folding end portions of the sheet over the central portion of the sheet along fold lines between the apexes of the aligned notches to form a bottom and overlapped flaps covering the bottom, stitching the ends of the flaps to the bottom, and turning the stitched assembly inside out to provide a pouch in the form of a generally rectangular strip having tapered ends and overlapped flaps which when pulled apart provide an open top closed bottom bag and which when longitudinally tensioned close the bag into a flat strip.

10. The method of claim 9 wherein the end tabs are also stitched to the ends of the flaps and bottom to project therefrom when the stitched assembly is turned inside out.

11. The method of claim 10 including the added step of folding over one edge of a flap to underlie the other flap in the finished pouch condition.

12. The method of claim 9 wherein the ends of the flaps and bottom portion are secured together by overlocked stitching.

13. The method of claim 12 wherein the overlocked stitching extends along the length of the free edges of the flap.

* * * * *